United States Patent [19]

Watson

[11] 3,985,822

[45] Oct. 12, 1976

[54] PROCESS FOR THE PRODUCTION OF POLY-N-BUTENES

[75] Inventor: James M. Watson, Big Spring, Tex.

[73] Assignee: Cosden Technology, Inc., Big Spring, Tex.

[22] Filed: Mar. 5, 1976

[21] Appl. No.: 664,141

[52] U.S. Cl. .................................. 260/683.15 B
[51] Int. Cl.² ........................................ C07C 3/18
[58] Field of Search ............ 260/683.15 R, 683.15 B

[56] References Cited
UNITED STATES PATENTS

| | | | |
|---|---|---|---|
| 2,657,246 | 10/1953 | Schneider et al. | 260/683.15 B |
| 2,970,179 | 1/1961 | Glaze | 260/683.15 B |
| 3,073,876 | 1/1963 | McMaster | 260/683.15 B |
| 3,119,884 | 1/1964 | Allen et al. | 260/683.15 B |
| 3,200,169 | 8/1965 | Nichols | 260/683.15 B |

Primary Examiner—C. Davis

[57] ABSTRACT

A process for the production of poly-n-butenes having a reduced content of isobutylene from isobutylene-containing $C_4$ feed stocks in a molecular weight range between 1,300 and 350 under controlled polymerization conditions, at a temperature range of 65°–115°F and in the presence of promoted aluminum chloride in quantity of 0.02 to 0.1% by weight based on total hydrocarbon feed, and the poly-n-butene products so produced.

5 Claims, No Drawings

PROCESS FOR THE PRODUCTION OF POLY-N-BUTENES

BACKGROUND OF THE INVENTION

This invention relates to the production of poly-n-butenes from a $C_4$ refinery gas feed stream which includes substantial polymerizable quantities of isobutylene, butene-1 and butene-2 as well as saturated $C_4$ components and some higher and lower hydrocarbon components, to maximize production of a low molecular weight poly-n-butene polymer in the range of 335 to 1300; and to poly-n-butene products so produced.

It is known in the art, shown by such U.S. Pat. Nos. as Allen, et al, 3,119,884 and Jackson 2,957,930 to form lower molecular weight polymers generally in the range of 400 to 1,000 from a refinery liquified $C_4$ gas feed stock, including isobutylene, butene-1 and cis and trans butene-2, using promoted dry aluminum chloride particles as a catalyst using hydrochloric acid or its water equivalent as the promoter. Such products as were formed contained large amounts of polyisobutylene containing smaller amounts of n-butenes present largely as impurity, co-polymerized with the isobutylene. Polymerization was generally carried out in a broad temperature range from about −20° F up to ambient temperatures such as 65° F non-critically, and with widely variable quantities of aluminum chloride catalyst, usually in continuous polymerization starting with about 0.08 to 5% by weight of the hydrocarbon treated. In practical polymerization of the butylenes component usually present in quantity of at least 3% by weight of the gas and usually comprised of from 10 to 70% isobutylene with about 10 to 30% of n-butenes, the remainder being saturated $C_4$ and minor quantities of $C_3$ and $C_5$ components. Such liquified refinery gases generally were fed continuously to a reactor while simultaneously supplying aluminum chloride catalyst and about 0.7 to 1 mole HCl per mole $AlCl_3$, and fresh feed together with several volumes of reactor effluent as the recycle to the reactor, whereby the catalyst concentration tended usually to be built up in the reactor to much larger quantities. The spent feed gas formed has most of the isobutylene content reacted, only a small quantity of the n-butenes polymerizing.

According to the present invention, it is found that when polymerizing at a very closely controlled temperature range of from 65° to 115° F (18.3°–46.1° C) using a promoted dry aluminum chloride catalyst in high dilution in a liquified $C_4$ hydrocarbon reaction medium containing predominantly isobutylenes, the amount of aluminum chloride being in the range of 0.035 up to 0.10% by weight, based upon the total hydrocarbon in the feed to the reactor, and being promoted with hydrochloric acid, a substantially increased amount of poly-n-butenes is formed, such poly-n-butenes ranging in composition with change of the reaction conditions in said ranges. Under these controlled conditions, the isobutylene content of the polymer formed is reduced.

The following are the chemical structures of the polymers which would be expected to form respectively from cis-trans butene-2, butene-1, and isobutylene, assuming the polymer is a pure molecule in which each of the monomeric units merely are repeated.

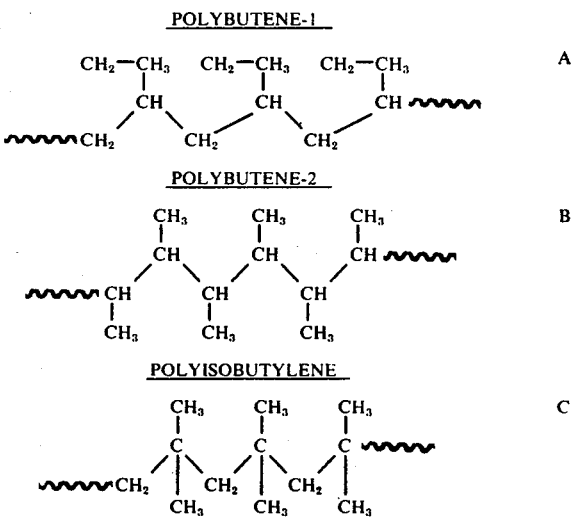

It is evident that the polymers differ structurally and consequently a pure polymer of each type would differ in properties from the others.

It is now found that polybutene polymers formed from predominantly isobutylene containing streams and having a molecular weight of above 1,350 will be substantially composed of about 98% or greater polyisobutylene, that is, repeating units of formula C above. Such result is obtained when using a low reaction temperature below about 60° to 70° F and low promoted catalyst component of 0.024 to 0.036% by weight of the hydrocarbon mixture, the promoter being hydrochloric acid in quantity of 0.7 to 1 mole per mole of the catalyst. Polymers formed to have a molecular weight progressively below 1,350 such as 1,300 according to the present invention, will have a significantly lesser quantities of polyisobutylene substantially greater quantities of poly-n-butene repeating units in its structure. In general for molecular weights ranging from 335 to 1,300, temperatures will range from 65° to 115° F with catalyst concentrations ranging from 0.05 to 0.1 wt. %. At a molecular weight as low as about 335 the polymer will have almost entirely the structure of formulas A and B above. The following Table I illustrates the most often used catalyst and temperature ranges with corresponding molecular weight and poly-n-butene content.

TABLE I

| MOLECULAR WEIGHT | REACTOR TEMP. RANGE | $AlCl_3$ Wt.%* | CONTENT POLY-N-BUTENE REPEATING UNITS |
|---|---|---|---|
| 335–400 | 100–115° F | 0.057–0.100 | 80% |
| 400–600 | 85–100° | 0.050–0.089 | 60–80 |
| 600–800 | 70–85° | 0.046–0.083 | 40–60 |
| 800–1000 | 65–75° | 0.035–0.062 | 20–40 |

*rel to total hydrocarbon

The preferred catalyst and temperature ranges for maximizing formation of poly-n-butene repeating units are given in the following Table II.

indicates it to be substantially entirely formed of 1- and 2-butene repeating units. The following table indicates in a polymerization run under the stated conditions that

TABLE IV

| Run No. | % Conversion of Isomers Charged* | | | | Calculated % Isobutylene Linkages in Product Assuming No Isomerization | % isobutylene Linkages in Product by IR |
|---|---|---|---|---|---|---|
| | ISO but | 1-but | 2-but trans but | 2-but cis but | | |
| 1 | 99.5 | 36.4 | 51.1 | 17.8 | 57.5 | 14.2 |
| 2 | 86.5** | 23.9** | 21.6** | 7.6** | 68.5 | 22.4 |
| 3 | 76.4 | 13.2 | — | — | 88.3 | 36.6 |

*Approximate composition of starting material: m— + i-butane: isobutylene: 1-butene: c— + t 2-butene + 3:2:2:3
**Based on feed

TABLE II

| MOLECULAR WEIGHT | REACTION TEMP. RANGE ° F. | AlCl₃ Wt. % |
|---|---|---|
| 335–400 | 110–115 | 0.08–0.1 |
| 400–600 | 95–100 | 0.07–0.089 |
| 600–800 | 80–85 | 0.06–0.083 |
| 800–1300 | 70–75 | 0.05–0.062 |

It is not intended to be limited to theory and the exact mechanism of the formulation of the three types of structures that may be present in the polymer chain is not known. However, these structures can be identified in the product quantitatively by NMR and IR spectroscopy by which the quantity of butylene components may be determined. The exact arrangement and quantity of the formula A and B components in the chain is not yet identified. Moreover, analysis before and after reaction of the feed gas shows that the isobutylene component is progressively withdrawn from the feed during the reaction, but this isomer does not build up correspondingly in the polymeric product formed.

The net effect is that polymers in the above mentioned molecular weight range contain fewer structural units of the formula C type above and are comparably more thermally stable. They are superior in many respects to isobutylene polymers of the same molecular weight, such as stable to decomposition by heating as well as by contact with chemical additives in the many common uses of polybutene polymers. It is found that these low molecular weight polybutene polymers having an increased poly-n-butene content are correspondingly more stable as lubricants and lubricant additives.

As will be seen from Tables I and II the optimum quantities of catalyst and the temperature varies from molecular weight to molecular weight. Although the catalyst is mixed in a very small quantity and the temperature is controlled in a very narrow range, these ranges for catalyst will overlap only slightly. However, each polymer grade generally is run in a distinct very narrow combined temperature and catalyst range that does not overlap so that each product formed is distinct as appears in Table I.

Surprisingly, the conversion of the isobutylene component in the feed does not correspond with the quantity of isobutylene appearing in that structure in the polymer formed. For instance, operating at the top of the temperature range given in Table II with 0.1 weight percent aluminum chloride, the feed containing substantially quantities of isobutylene as well as 1- and 2-butenes, will be largely denuded of isobutylene after reaction. However, the analysis of the polymer formed under these conditions by NMR and IR spectroscopy the quantity of isobutylene and butenes consumed from the charge does not correspond with the quantities analyzed in the product polymer.

The following examples illustrate the practice of this invention:

EXAMPLE I

A liquified $C_1$–$C_5$ feed stock comprising cracked petroleum refinery gases, having the composition of 14 mol percent butene-1, 10 mol percent of cis and trans butene-2, 15 mol percent of isobutylene, 56 mol percent butanes and the balance $C_3$ and $C_5$ hydrocarbon impurities, is passed at a ratio of about 42 gallons a minute in dried liquified form to a reactor carefully maintained at a temperature between 95° to 100° F, the liquified gas feed being carefully adjusted to this temperature and then intimately mixed with 0.85% by weight of aluminum chloride particles containing 0.8 mole of concentrated hydrochloric acid/mole $AlCl_3$, the quantity of catalyst being based on the quantity of hydrocarbon in the feed and being continuously adjusted in the recycle to the reactor to maintain the same substantially constant. The reaction product was withdrawn continuously at a rate corresponding to the feed, the total recycle being in approximate ratio of 8:1 recycle to feed with a total quantity of 300 gpm flowing as recycle. The spent reaction fluid after separation of polymer was analyzed to show that 99.5% of the total isobutylene originally present was removed from the reaction mixture, 36.4% of the butene-1, 17.8% of cis-butene-2 and 51.1% of the trans-butene-2. All percentages being based on the quantity of the monomer initially present in the feed to the reactor. The recovered polymer had an average molecular weight of about 425. It is therefore calculated that the final product should contain theoretically 63.8% isobutylene linkages in the polymer formed, assuming no isomerization. The actual quantity of isobutylene present and actually found by ir analysis in the polymer was 21.3% by weight. This indicates substantial isomerization of the isobutylene takes place either in the polmer as formed or in the feed before polymerization, since practically all of the isobutylene was withdrawn from the feed during the reaction and very little appears in the final feed.

EXAMPLE II

The reaction of Example I was repeated except that the catalyst quantity was increased to 0.10%, again promoted with 0.1% hydrochloric acid based thereon and the temperature was increased and maintained in the range of 110° to 115° F. Again, it was found that 99.5% of isobutylene in the feed had reacted together with 39.2% of 1-butene, 18.5% of cis butene-2 and 53.4% of trans butene-2. Again it was calculated that 62.5% of isobutylene should have appeared in the reaction product but actual IR analysis showed only 7.4% of isobutylene linkages to be present in the polymer which had a molecular weight of 350. There were substantially fewer isobutylene linkages and the polymer is substantially a "straight" chain polymer of the A and B formulas above.

EXAMPLE III

The reaction of Example I was repeated holding the temperature this time to the range of 80° – 85° F and the catalyst at above 0.075 – 0.083% by weight of the feed. It is now found that the precent conversion of the isobutylene in the feed was 86.5%, butene-1 content was 23.9%, the cis-butene-2 content 7.6% and the trans-butene-2 21.6% of the respective initial contents of the feed. It was calculated that the polymer should contain 68.5% of the isobutylene linkages and be present in the polymer as such, but it was found that only 22.4% of the isobutylene linkages were present. The polymer had an average molecular weight of 625.

EXAMPLE IV

The reaction is again repeated this time holding the catalyst content to 0.055 – 0.62% and the reactor at a temperature of 70° – 75° F. It is found that the polymer had 65% of isobutylene linkages and an average molecular weight of 975.

Certain modifications will occur to those skilled in the art and it is intended that this description be regarded as exemplary and not limiting.

What is claimed is:

1. The method of forming liquid polybutene polymer having a molecular weight in the range of 335 to 1,300 and having an increased poly-n-butene content, said method comprising polymerizing a $C_3 - C_5$ liquified feed gas containing at least 3% of butylenes comprised of 10 to 70% isobutylenes and 10 to 30% n-butenes, at a temperature in the range of 65° to 115° F in the presence of from about 0.035 to 0.1% by weight of said hydrocarbon of dry aluminum chloride particles promoted with a minor quantity of a promoter.

2. The method as defined in claim 1 wherein the reaction temperature is controlled within the range of 65° – 75° F and the quantity of catalyst is from about 0.035 to 0.062% based on said hydrocarbon promoted with a minor quantity based on said catalyst of hydrochloric acid.

3. The method as defined in claim 1 wherein the reaction temperature is controlled within the range of 70° – 85° F and the quantity of catalyst is from about 0.046 to 0.083% based on said hydrocarbon promoted with a minor quantity based on said catalyst of hydrochloric acid.

4. The method as defined in claim 1 wherein the reaction temperature is controlled within the range of 85° – 100° F and the quantity of catalyst is from about 0.050 to 0.089% based on said hydrocarbon promoted with a minor quantity based on said catalyst of hydrochloric acid.

5. The method as defined in claim 1 wherein the reaction temperature is controlled within the range of 100° – 115° F and the quantity of catalyst is from about 0.057 to 0.10% based on said hydrocarbon promoted with a minor quantity based on said catalyst of hydrochloric acid.

* * * * *